United States Patent
Al-Dhfyan et al.

(10) Patent No.: US 9,119,856 B1
(45) Date of Patent: Sep. 1, 2015

(54) METHOD FOR TREATING CANCER USING A DIHYDROPYRIMIDINE DERIVATIVE

(71) Applicants: KING SAUD UNIVERSITY, Riyadh (SA); KING FAISAL SPECIALIST HOSPITAL AND RESEARCH CENTER, Riyadh (SA)

(72) Inventors: Abdullah Omar Al-Dhfyan, Riyadh (SA); Mashooq Ahmad Bhat, Riyadh (SA)

(73) Assignees: KING SAUD UNIVERSITY, Riyadh (SA); KING FAISAL SPECIALIST HOSPITAL AND RESEARCH CENTER, Riyadh (SA)

( * ) Notice: Subject to any disclaimer, the term of this patent is extended or adjusted under 35 U.S.C. 154(b) by 0 days.

(21) Appl. No.: 14/666,302

(22) Filed: Mar. 23, 2015

(51) Int. Cl.
  *A61K 31/455* (2006.01)
  *C07D 239/22* (2006.01)
  *C07D 403/12* (2006.01)
  *A61K 31/513* (2006.01)
  *A61K 45/06* (2006.01)
  *A61K 31/505* (2006.01)
  *C07D 403/04* (2006.01)

(52) U.S. Cl.
  CPC ............. *A61K 31/513* (2013.01); *A61K 31/505* (2013.01); *A61K 45/06* (2013.01); *C07D 239/22* (2013.01); *C07D 403/04* (2013.01); *C07D 403/12* (2013.01)

(58) Field of Classification Search
  CPC ... A61K 31/513; A61K 31/505; A61K 45/06; C07D 239/22; C07D 403/12; C07D 403/04
  See application file for complete search history.

(56) References Cited

U.S. PATENT DOCUMENTS 7,687,511 B2   3/2010  Pullela et al.
2005/0282838 A1  12/2005  Ramchandani et al.

FOREIGN PATENT DOCUMENTS

WO   WO 2007/101213 A2   9/2007

OTHER PUBLICATIONS

Henrich et al., "New inhibitors of ABCG2 identified by high-throughput screening," Mol Cancer Ther, 2007, 3271-8.

*Primary Examiner* — Savitha Rao
(74) *Attorney, Agent, or Firm* — Richard C. Litman

(57) ABSTRACT

A method of treating cancer using a dihydropyrimidine derivative includes administering to a patient a therapeutically effective amount of a dihydropyrimidine derivative having the following formula:

FORMULA 1

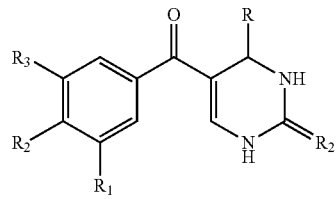

wherein:
  $R_2$ is S or O and
  R, $R_1$, $R_3$, and $R_4$ each independently represent hydrogen, optionally substituted straight-chain or branched C1 to C7 alkyl, halogen, optionally substituted haloalkyl, alkoxy or haloalkoxy in which the alkyl is straight-chain or branched C1-C4 alkyl and the halo derivatives are mono, di, tri or poly halosubstituted, the optional substituents including halogen, amino, substituted amino, C1-C4 alkyl, halo (C1-C4) alkyl, alkoxy or haloalkoxy having C1-C4 alkyl group, or R, $R_1$, $R_3$, and $R_4$ each independently represent aryl, substituted aryl, heteroaryl, or substituted heteroaryl, the substituents including halogen, alkyl, haloalkyl, alkoxy, haloalkoxy, alkylthio, alkylamino, aryl, heteroaryl, aryloxy, haloaryloxy, arylthio, or arylamino;

or a pharmaceutically acceptable salt thereof.

11 Claims, 5 Drawing Sheets

METHOD FOR TREATING CANCER USING A DIHYDROPYRIMIDINE DERIVATIVE

BACKGROUND OF THE INVENTION

1. Field of the Invention

The present invention relates to use of compounds for treating cancer, and particularly to dihydropyrimidine derivatives for targeting cancer stem cells.

2. Description of the Related Art

Drug discovery programs for oncology typically select compounds which have a predilection for inducing cytotoxic effects in cancer cell lines versus non-cancer cells and for inhibiting the growth of transplanted cancer cells in the flanks of immunocompromised mice. Unfortunately, inducing cytotoxic effects in vitro and inhibition of tumor growth in vivo is not the end story for curing cancer in preclinical models. This is, at least in part, due to the presence of cancer stem cells (CSCs), a small sub-type of cells that are relatively resistant to therapy and able to repopulate in vivo. It is believed that tumors are organized in a cellular hierarchy driven by cancer stem cells (CSCs). The cancer stem cell (CSC) hypothesis postulates that tumors are maintained by a self-renewing CSC population that is also capable of differentiating into non-self-renewing cell populations that constitute the bulk of the tumor. This hypothesis has fundamental implications for oncology and clinical implications for the early detection, prevention, and treatment of cancer. There are now numerous studies which have identified cancer stem cells in leukemia, breast, brain, lung, colon, and other cancers. To cause relapse, CSCs must have survived primary treatment. A number of factors may be responsible for this survival of CSCs, including stem cell quiescence, protected niche environment, up-regulated expression of xenobiotic efflux pumps, enhanced anti-apoptotic and DNA repair pathways. The first identification of breast cancer stem cells was defined by the combined expression of cell surface markers CD44+/CD24−/low/lin−. As few as 200 of these cells generated tumors in NOD/SCID mice, whereas 20,000 cells that did not display this phenotype failed to generate tumors. Later, studies suggested that aldehyde dehydrogenase 1 (ALDH-1), a detoxifying enzyme responsible for oxidation of retinol to retinoic acid, may be a more potent marker of breast CSCs. ALDH-1-positive breast CSCs can induce tumor formation with as few as 500 cells. Breast cancer cells that expressed ALDH-1 were more likely to be estrogen receptor (ER) negative, progesterone receptor (PR) negative, and human-epidermal growth factor receptor type 2 (HER-2) positive, and frequently developed distant metastases. ALDH-1-positive cells are resistant to conventional chemotherapy with paclitaxel and epirubicin. Previous studies have shown that adult stem cells can be identified by a side population (SP) phenotype. A SP isolated from the breast cancer cell line MCF7 was found to represent small percentage of the total cell line and it contained the tumorigenic fraction, as demonstrated by transplantation experiments in NOD/SCID mice xenografts. This fraction was also able to reconstitute the initial heterogeneity of the cell line. In breast tumors, the use of neoadjuvant regimens showed that conventional chemotherapy could lead to enrichment in CSCs in treated patients as well as in xenografted mice. This suggests that many cancer therapies, while killing the bulk of tumor cells, may ultimately fail because they do not eliminate CSCs, which survive to regenerate new tumors. Thus, there remains an urgent need for new pharmaceutical compounds and compositions to effectively eradicate and target cancer stem cells.

ATP binding cassette (ABC) transporters form one of the largest transmembrane protein families. These proteins use cellular ATP to drive the transport of various substrates across cell membranes including drugs, metabolites and other compounds. Human ABCG2 is the second member of the G subfamily of ABC transporters. ABCG2 was first cloned from doxorubicin-resistant human MCF-7 breast cancer cells and named as breast cancer resistance protein (BCRP). ABCG2 is sharply down-regulated during hematopoietic stem cell differentiation and is expressed at a low level in mature cells compared with progenitor cells. The highly regulated expression of ABCG2 suggests that ABCG2 may play a regulatory role in maintaining stem cells in an undifferentiated state. A RNA interference approach showed that the suppression of ABCG2 could significantly inhibit cancer cell proliferation. Furthermore, the blocking of ABCG2 function by fumitremorgin C, a chemical inhibitor, also inhibited cell proliferation via the prolonged G0/G1 interval. These data suggest that ABCG2 may contribute to cancer cell proliferation. Taking into account that the SP phenotype is mainly mediated by ABCG2 and the conserved expression of ABCG2 in stem cells, it is conceivable that ABCG2 may serve as a novel biomarker of CSCs. Since ABCG2 functions as a high capacity transporter with a wide range of substrates including various chemotherapy drugs, it has been shown to participate in the multidrug resistance of tumors.

Thus, a method for treating cancer solving the aforementioned problems is desired.

SUMMARY OF THE INVENTION

A method of treating cancer using a novel dihydropyrimidine derivative includes administering to a subject in need thereof a composition including a therapeutically effective amount of a dihydropyrimidine derivative and a pharmaceutically acceptable carrier, the dihydropyrimidine derivative being a compound of Formula I:

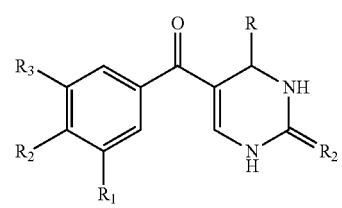

FORMULA I wherein:

$R_2$ is S or O and

R, $R_1$, $R_3$, and $R_4$ each independently represent hydrogen, optionally substituted straight-chain or branched C1 to C7 alkyl, halogen, optionally substituted haloalkyl, alkoxy or haloalkoxy in which the alkyl is straight-chain or branched C1-C4 alkyl and the halo derivatives are mono, di, tri or poly halosubstituted, the optional substituents for the optionally substituted alkyl, haloalkyl, alkoxy, or haloalkoxy groups including halogen, amino, substituted amino, C1-C4 alkyl, halo (C1-C4) alkyl, alkoxy or haloalkoxy having 1 to 4 carbon atoms in the alkyl group, or R, $R_1$, $R_3$, and $R_4$ each independently represent aryl, substituted aryl, heteroaryl, or substituted heteroaryl, the substituents of the optionally substituted aryl and heteroaryl groups including halogen, alkyl, haloalkyl, alkoxy, haloalkoxy, alkylthio, alkylamino, aryl, heteroaryl, aryloxy, haloaryloxy, arylthio, or arylamino;

or a pharmaceutically acceptable salt thereof.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
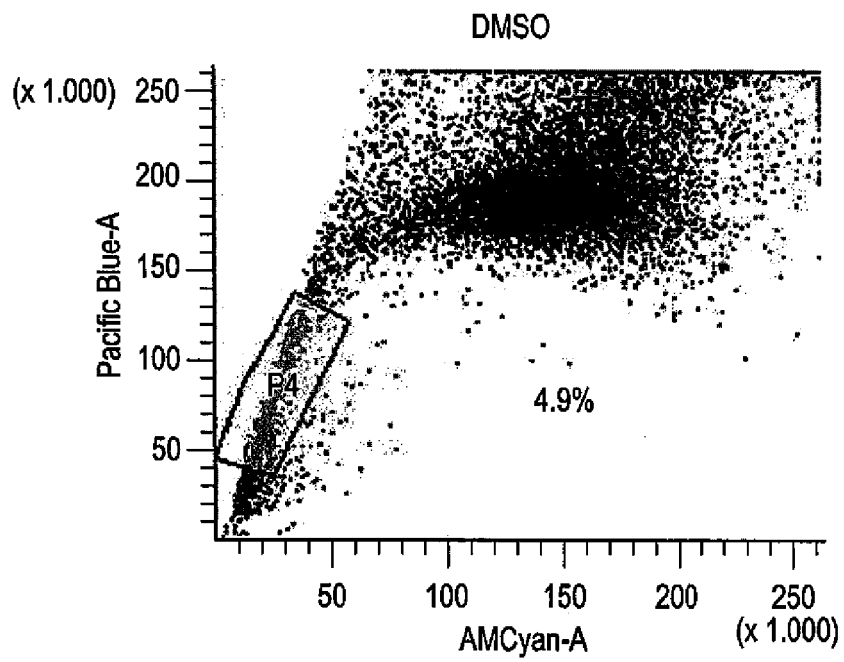
FIG. 1A is a scatter plot showing results of side population analyses of MCF-7 cells treated by dimethyl sulfoxide (DMSO) only.

A method of treating cancer using a novel dihydropyrimidine derivative includes administering to a patient in need thereof a composition including a therapeutically effective amount of a dihydropyrimidine derivative and a pharmaceutically acceptable carrier, wherein the dihydropyrimidine derivative is a compound of Formula

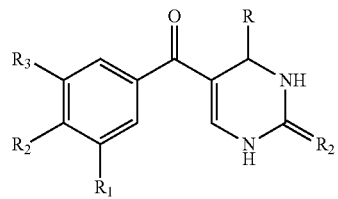

FORMULA I wherein:

$R_2$ is S or O; and

R, R1, R3, and R4 each independently represent hydrogen, optionally substituted straight-chain or branched C1 to C7 alkyl, halogen, optionally substituted haloalkyl, alkoxy or haloalkoxy in which the alkyl is straight-chain or branched C1-C4 alkyl and the halo derivatives are mono, di, tri or poly halosubstituted, the optional substituents for the optionally substituted alkyl, haloalkyl, alkoxy, or haloalkoxy groups including halogen, amino, substituted amino, C1-C4 alkyl, halo (C1-C4) alkyl, alkoxy or haloalkoxy having 1 to 4 carbon atoms in the alkyl group, or R, R1, R3, and R4 each independently represent aryl, substituted aryl, heteroaryl, or substituted heteroaryl, the substituents of the substituted aryl and heteroaryl groups including halogen, alkyl, haloalkyl, alkoxy, haloalkoxy, alkylthio, alkylamino, aryl, heteroaryl, aryloxy, haloaryloxy, arylthio, or arylamino;

or a pharmaceutically acceptable salt thereof.

A pharmaceutically acceptable salt includes any non-toxic salt of the present compounds, which are generally prepared by reacting the free acid with a suitable organic or inorganic base. Examples of such salts include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methyinitrate, methylsulfate, mucate, napsylate, nitrate, oleate, oxalate, pamaote, palmitate, panthothenate, phosphate/diphosphate, polygalacturonate, potassium, salicylate, sodium, stearate, subacetate, succinate, tannate, tartrate, teoclate, tosylate, triethiodide, valerate.

Acids with which addition salts can be formed can include hydrohalic acids such as for example, hydrochloric acid and hydrobromic acid, and also phosphoric acid, nitric acid, monofunctional and bifunctional carboxylic acids hydroxy carboxylic acids, such as, acetic acid, maleic acid, succinic acid, fumaric acid, tartaric acid, salicylic acid, sorbic acid and lactic acid, as well as sulphonic acids such as, p toluenesulphonic acid and naphthaline-1,5-disulphonic acid.

The dihydropyrimidine derivatives can include a 5-benzoyl-3,4-dihydropyrimidin-2(1H)-one/thione compound or a pharmaceutically acceptable salt thereof. For example, the dihydropyrimidine derivatives can include 4-(4-ethoxyphenyl)-5-(3,4,5-trimethoxybenzoyl)-3,4-dihydropyrimidin-2 (1H)-one, referred to as DHP-5 herein, having the following structural formula below (FORMULA II):

FORMULA II

The dihydropyrimidine derivatives can be used as an active ingredient of pharmaceuticals for the treatment of proliferative diseases, such as cancer. It is widely believed that tumor is initiated and driven by cancer stem cells (CSCs). CSCs are also believed to be responsible for multi-drug chemoresistance and to lead to cancer relapse. It is believed that there is a close link between ATP-binding cassette sub-family G member 2 (ABCG2) transporters and CSCs. ABCG2+ tumor cells may hence represent a unique population of CSCs. The expression of this chemoresistant efflux transporter in CSC populations can confer these cells intrinsic resistance to many commonly used or conventional antitumor agents and may be the root cause of tumor recurrence.

The dihydropyrimidine derivatives are small molecule compounds that can treat cancer by, for example, targeting cancer-initiating or cancer stem cells, such as ABCG2+ tumor cells. The dihydropyrimidine derivatives can be anti-mitotic agents, i.e., inhibitors of mitotic cell division. The dihydropyrimidine derivatives can selectively target CSCs through inhibition of side population (SP) cells, via ABCG2 modulations. The dihydropyrimidine derivatives can inhibit ABCG2. The dihydropyrimidine derivatives can modulate ABCG2 and its related pathways to treat resistant cancers from solid and/or hematological origin. The dihydropyrimidine derivatives can target cancer stem cells (from any possible phenotype) including but not limited to, sphere forming cells, colony forming cells, ALDH positive cells, side population cells, and CD44HIGH/CD24LOW cells.

Figure 5:
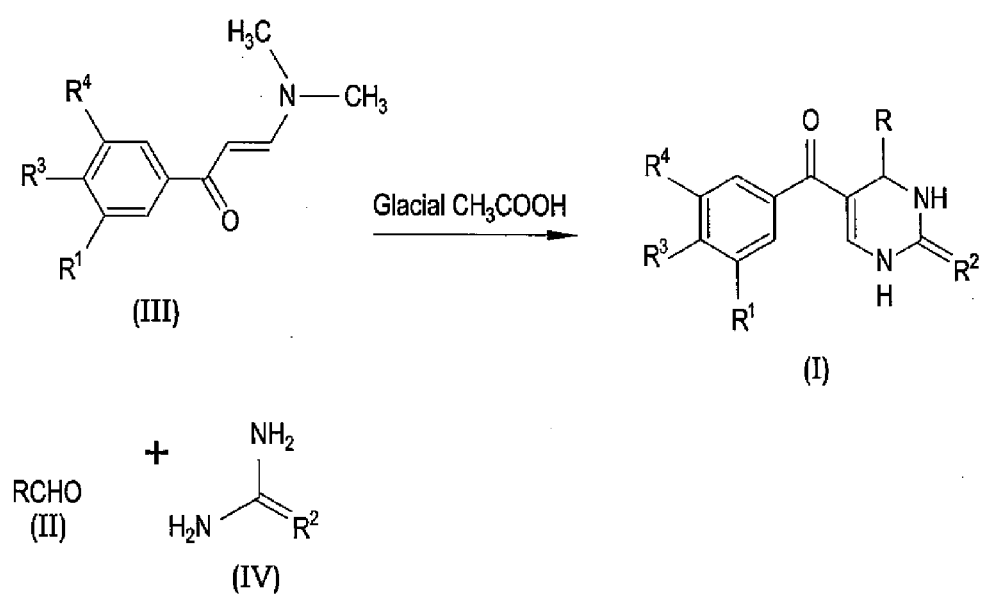
FIG. 5 is an exemplary reaction scheme for synthesis of the dihydropyrimidine derivatives according to the present invention.

FIG. 5 depicts a reaction scheme by which exemplary dihydropyrimidine derivatives can be prepared. Referring to FIG. 5, equivalent molar amounts of aldehyde II, enaminone III, and urea/thiourea IV can be reacted in the presence of glacial acetic acid ($CH_3COOH$) (10 mL) to produce the dihydropyrimidine derivative of Formula I, where, $R_1$, $R_2$, $R_3$, and $R_4$ represent the molecules disclosed above. Preferably the mixture is heated to a temperature of between about 80° C. and 120° C. for several hours. The resulting product can be purified using techniques well-known in the art, including crystallization, precipitation, chromatography on silica gel, extraction, and high performance chromatography.

As used herein, the terms "conventional antitumor agent," or "conventional cancer therapeutic drug" refer to any conventional or commonly used therapeutic agents (e.g., chemotherapeutic compounds and/or molecular therapeutic compounds), radiation therapies, or surgical interventions, used in the treatment of cancer (e.g., in mammals).

As used herein, the terms "drug" and "chemotherapeutic agent" refer to pharmacologically active molecules that are used to diagnose, treat, or prevent diseases or pathological conditions in a physiological system (e.g., a subject, or in vivo, in vitro, or ex vzvo cells, tissues, and organs). Drugs act by altering the physiology of a living organism, tissue, cell, or in vitro system to which the drug has been administered. It is intended that the terms "drug" and "chemotherapeutic agent" encompass anti-hyperproliferative and antineoplastic compounds as well as other biologically therapeutic compounds. As used herein the term "prodrug" refers to a pharmacologically inactive derivative of a parent "drug" molecule that requires biotransformation {e.g., either spontaneous or enzymatic) within the target physiological system to release, or to convert (e.g., enzymatically, mechanically, electromagnetically, etc.)

The terms "subject," "patient" and "host" refer to humans and/or animals.

The term "treatment" used herein refers to taking drugs and compounds to reach any therapeutic values and clinical outcomes by any possible way of administration.

As used herein, the term "in vitro" refers to an artificial environment and to processes or reactions that occur within an artificial environment. In vitro environments can consist of, but are not limited to, test tubes and cell cultures. The term "in vivo" refers to the natural environment (e.g., an animal or a cell) and to processes or reactions that occur within a natural environment.

As used herein, the term "cell culture" refers to any in vitro culture of cells from either normal or cancer source.

The relationship of compound structure and compound activity of various Formula I compounds, i.e., 5-benzoyl-3,4-dihydropyrimidin-2(1H)-one/thione compounds, on inhibition of side population cancer stem cells was studied. The various 5-benzoyl-3,4-dihydropyrimidin-2(1H)-one/thione compounds and the corresponding inhibition activity are provided below in Table 1.

TABLE 1

| Compounds | R | $R_1$ | $R_2$ | Side Population Inhibition (%) at 10 µM |
|---|---|---|---|---|
| DHP-1 | Phenyl | —$OCH_3$ | O | 0 |
| DHP-2 | 4-Chlorophenyl | —$OCH_3$ | O | 643 |
| DHP-3 | 4-Nitrophenyl | —$OCH_3$ | O | 64 |
| DHP-4 | 3,4-Dimethoxyphenyl | —$OCH_3$ | O | 70.5 |
| DHP-5 | 4-Ethoxyphenyl | —$OCH_3$ | O | 58.82 |
| DHP-6 | Phenyl | H | S | 70 |
| DHP-7 | 4-Chlorophenyl | H | S | Not Determined |
| DHP-8 | 4-Nitrophenyl | H | S | 50 |
| DHP-9 | 3,4-Dimethoxyphenyl | H | S | 0 |

The newly synthesized compounds DHP (1-9) were evaluated for side population inhibition on lovo colon cancer cells (%) at 10 µM concentration. Out of this series (DHP 1-9), four compounds were found to be very effective, namely DHP-4, DHP-6, DHP-2 and DHP-3, when measured at 10 µM concentration. Compounds DHP-5 and DHP-8 were moderately active as indicated by a low value of side population inhibition (%). Most of the newly synthesized dihydropyridine compounds DHP (1-9) showed significant activity against side population inhibition (%). It was noted that most of the compounds which include a methoxy group at $R_1$ were active. The methoxy group seems to help the molecule to align in protein pocket. Compounds with an oxygen atom at $R_2$ were also active. It seems that the oxygen atom at position $R_2$ also plays some important role in binding with protein pocket. Compound DHP-6, which contains hydrogen at $R_1$ and sulphur atom at $R_2$ has shown unexpectedly significant activity.

From these results it can be concluded that compound DHP-4 was found to be the most active compound of the series. Methoxy group at $R_1$ and oxygen atom at $R_2$ plays an important role in binding with the functional protein.

As discussed in further detail below, the present inventors have found that DHP-5 is a more potent inhibitor of side population cells than reference drug Verapamil. Furthermore, DHP-5 treatment facilitated blocking self-renewal ability of breast cancer cells in a dose dependent manner. DHP-5 induced apoptosis and blocked cell proliferation in vitro and showed superior efficacy compared to reference drug Doxorubicin in advanced animal models of breast and colon cancer without any sign of general toxicity.

Treatment of cancer/cancer stem cells may be accomplished by the dihydropyrimidine derivatives alone, e.g., as a stand-alone therapeutic approach, or in combination with other treatment as an adjunctive therapy. It has been found that the dihydropyrimidine derivatives can provide an additive or synergistic effect with other types of chemotherapeutic agents. The dihydropyrimidine derivatives and/or analogs thereof, therefore, may be used with chemotherapeutic agents either for malignant or benign tumors Secondary therapeutic agents that can be used with one or more of the present compounds include, but are not limited to, doxorubicin, vinblastine, paclitaxel, vincristine, Vinorelbine, Topotecan, Carboplatin, Cisplatin, Pemetrexed, Irinotecan, Gemcitabine, Gefitinib, Erlotinib, Etoposide, cyclophoshamide, flurouracil, Mercaptopurine, Fludarabine, Ifosfamide, Procarbazine, mitoxantrone. A listing of additional chemotherapeutic agents and the dosage as used herein can be found in 2002 Update of Recommendations for the Use of Chemotherapy and Radiotherapy Protectants: Clinical Practice Guidelines of the American Society of Clinical Oncology, J Clin Oncol. 2002 Jun. 15; 20 (12):2895-903.

The dihydropyrimidine derivatives for treating cancer can be administered to a patient in need thereof. For example, the dihydropyrimidine derivatives can be used to treat a patient suffering from diseases with a proliferative nature, such as cancer. The cancer can include leukemia, breast cancer, brain cancer, lung cancer, colon cancer, or other cancers. The cancer can be resistant to conventional anti-cancer therapies. The cancer can be from solid and/or hematological origin. The cancer can be a solid or non-solid tumor.

The dihydropyrimidine derivatives or pharmaceutical compositions including the present compounds can be administered to a subject by any suitable route. For example, the compositions can be administered orally (including bucally and sublingually), nasally, rectally, parenterally, intracisternally, intra vaginally, intraperitoneally, topically and transdermally (as by powders, ointments, or drops). The term "parenteral" administration as used herein refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation also is contemplated, including, for example, embedding a composition of the disclosure in the body such as, for example, in a tissue, in the abdominal cavity, under the splenic capsule, brain, or in the cornea. Accordingly, the route of administration can include intranasal administration; oral administration; inhalation administration; subcutaneous administration; transdermal administration; intradermal administration; intra-arterial administration, with or without occlusion; intracranial administration; intraventricular administration; intravenous administration; buccal administration; intraperitoneal administration; intraocular administration; intramuscular administration; implantation administration; topical administration, intratumor administration and/or central venous administration.

Also provided is a pharmaceutical composition including one or more of the dihydropyrimidine derivatives for treating cancer. To prepare the pharmaceutical composition, one or more of the dihydropyrimidine derivatives or a salt thereof, as the active ingredient, is intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents and the like; for solid oral preparations, suitable carriers and additives include starches, sugars, diluents, granulating agents, lubricants, binders, disintegrating agents and the like. For parenteral use, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. Accordingly, the pharmaceutically acceptable carrier can include alcohol, dimethyl sulfoxide (DMSO), a physiological saline, a lipid based formulation, a liposomal formulation, a nanoparticle formulation, a micellar formulation, a water soluble formulation, a biodegradable polymer, an aqueous preparation, a hydrophobic preparation, a lipid based vehicle, or a polymer formulation.

The dihydropyrimidine derivatives of the present disclosure also can be administered in the form of liposomes. As is known in the art, liposomes generally are derived from phospholipids or other lipid substances. Liposomes are formed by mono- or multi-lamellar hydrated liquid crystals that are dispersed in an aqueous medium. Any nontoxic, physiologically acceptable, and metabolizable lipid capable of forming liposomes can be used. The present compositions in liposome form can contain, in addition to a compound of the present disclosure, stabilizers, preservatives, excipients, and the like. The preferred lipids are the phospholipids and the phosphatidyl cholines (lecithins), both natural and synthetic.

Pharmaceutical compositions for parenteral injection can include pharmaceutically acceptable sterile aqueous or nonaqueous solutions, dispersions, suspensions, or emulsions, as well as sterile powders for reconstitution into sterile injectable solutions or dispersions just prior to use. Examples of suitable aqueous and nonaqueous carriers, diluents, solvents, or vehicles include water ethanol, polyols (such as, glycerol, propylene glycol, polyethylene glycol, and the like), and suitable mixtures thereof, vegetable oils (such, as olive oil), and injectable organic esters such as ethyl oleate. Proper fluidity can be maintained, for example, by the use of coating materials such as lecithin, by the maintenance of the required particle size in the case of dispersions, and by the use of surfactants.

The present compositions can include adjuvants such as preservatives, wetting agents, emulsifying agents, and dispersing agents. Prevention of the action of microorganisms can be ensured by the inclusion of various antibacterial and antifungal agents, for example, paraben, chlorobutanol, phenol sorbic acid, and the like. It also may be desirable to include isotonic agents such as sugars, sodium chloride, and the like. Prolonged absorption of the injectable pharmaceutical form can be brought about by the inclusion of agents which delay absorption, such as aluminum monostearate and gelatin. In some cases, in order to prolong the effect of the drug, it is desirable to slow the absorption of the drug from subcutaneous or intramuscular injection. This result can be accomplished by the use of a liquid suspension of crystalline or amorphous materials with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by inhalation or insufflation. The active compound is mixed under sterile conditions with a pharmaceutically acceptable carrier and any needed preservatives, buffers, or propellants which may be required. Ophthalmic formulations, eye ointments, powders, and solutions also are contemplated as being within the scope of this disclosure. The composition can be presented in a form suitable for daily, weekly or monthly administration. The pharmaceutical compositions herein will contain, per dosage unit, e.g., tablet, capsule, powder, injection, teaspoonful, suppository and the like, an amount of the active ingredient necessary to deliver an effective dose.

A therapeutically effective amount of the dihydropyrimidine derivatives or an amount effective to treat cancer may be determined initially from in vivo assays described herein and adjusted for specific desired dihydropyrimidine derivatives using routine methods. The therapeutically effective amount of the dihydropyrimidine derivatives can be from about 1 mg/kg/day to about 200 mg/kg/day.

The following examples illustrate the present teachings.

EXAMPLE 1

Cell line and Tissue Culture

LOVO colon cancer cells and MCF-7 breast cancer cell lines were purchased from the American Type Culture Collection. LOVO Cells were cultured in RPMI, and MDA-MB-468 cells were cultured in DMEM. Both media supplemented with 10% FBS (Cambrex Bio Science), 100 IU/mL penicillin and 100 mg/mL streptomycin. Cell viability was assessed by trypan blue exclusion analysis. Cell numbers were determined by using a hemacytometer.

EXAMPLE 2

Flow Cytometric Analysis of Cellular DNA Content $2\times10^6$ cells were fixed in 1 ml ethanol (70%) for 60 min. at room temperature. Harvested cells were resuspended in 1 ml Na citrate (50 mM) containing 250 µg RNase A and incubated at 50° C. for 60 min. Next, cells were resuspended in the same buffer containing 4 µg propidium iodine (PI) and incubated for 30 min. before being analyzed by flow cytometry (Becton Dickinson, San Jose, Calif., USA). The percentage of cells in various cell cycle phases was determined by using Cell Quest Pro software (Becton Dickinson).

DNA cell cycle analysis of untreated and DHP-5 treated MCF-7 cells showed increased accumulation of treated cells in G2+M mitosis phase. The histogram distribution demonstrated the anti-cancer effect of DHP-5.

EXAMPLE 3

Side Population Staining by DYECYCLE Violet Stain

For DCV staining, cells were pelleted and suspended in DMEM cell culture medium at a concentration of $1*10^6$ cells/ml. DCV (Invitrogen Molecular Probes®, Eugene, Oreg.) was added at a final staining concentration of 10 µM, as this concentration gave optimal separation between SP and non SP cells. PI stained was used to exclude dead cells. Functionally, to gate only side population cells, Verapamil 200 µM or FTC 10 µg/ml was used. All analyses were performed on a FACS LSRII (BD Biosciences). Debris and cell clusters were excluded during side-scatter and forward-scatter analyses.

Figure 1B:
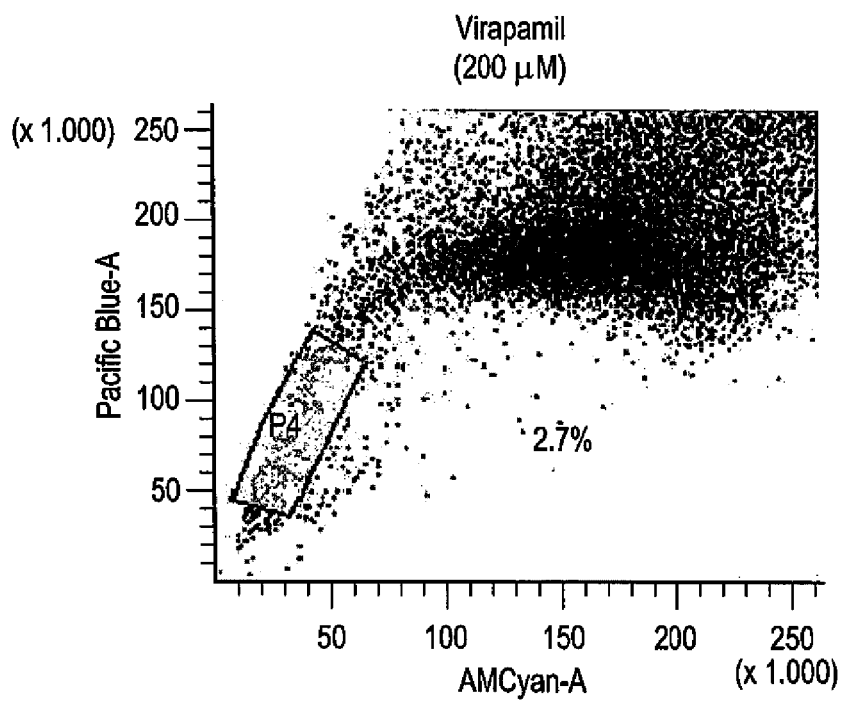
FIG. 1B is a scatter plot showing results of side population analyses of MCF-7 cells treated by side population inhibitor reference drug Verapamil 200 µM.
Figure 1C:
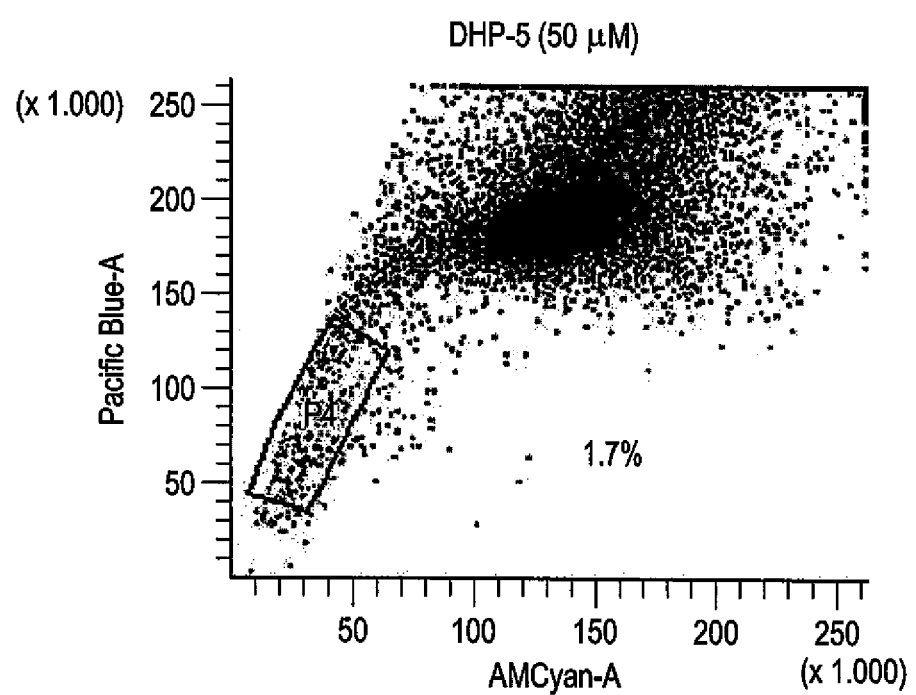
FIG. 1C is a scatter plot showing results of side population analyses of MCF-7 cells treated with treated by DHP-5 (50 µM).

A side population analysis of MCF-7 breast cancer cells treated with DMSO-only control (FIG. 1a), side population inhibitor reference drug Verapamil 200 µM (FIG. 1B), FTC 10 µg/ml, and DHP-5 (50 (FIG. 1C), 75 and 100 µM) showed a more potent inhibitory effect of DHP-5 on side population cancer stem cells than reference drug Verapamil.

Figure 4:
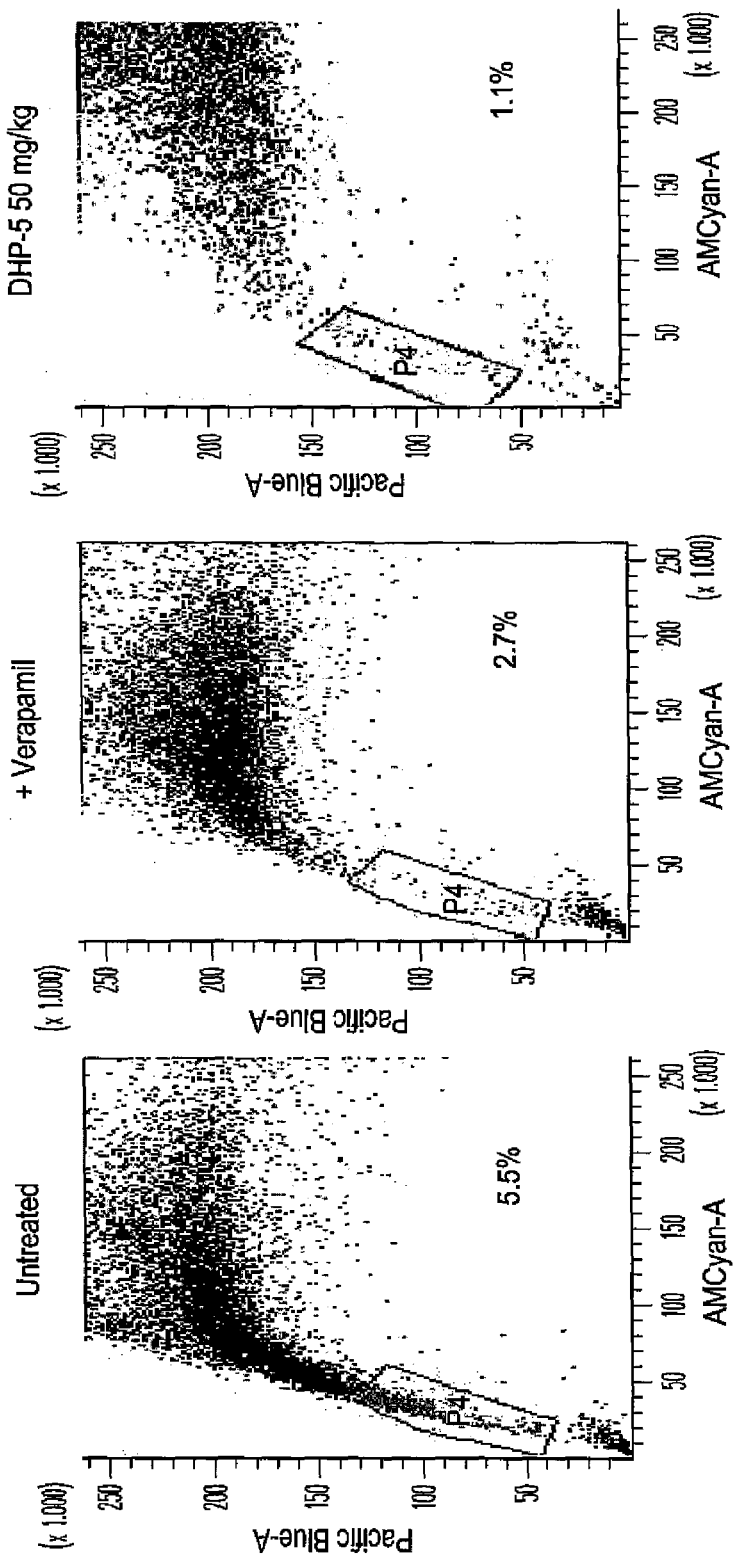
FIG. 4A is a scatter plot showing results of side population analyses of tumor derived cells of LOVO xenograft that were untreated.
FIG. 4B is a scatter plot showing results of side population analyses of tumor derived cells of LOVO xenograft that were treated with side population inhibitor reference drug Verapamil 200 µM.
FIG. 4C is a scatter plot showing results of side population analyses of tumor derived cells of LOVO xenograft of the animals that were treated by DHP-5 50 mg/kg for 14 days.

A side population analysis of tumor derived cells of LOVO xenograft that were untreated (FIG. 4A), treated with side population inhibitor reference drug Verapamil 200 µM (FIG. 4B), and side population analysis of tumor cells derived from animals treated by DHP-5 50 mg/kg for 14 days. (FIG. 4C) showed a more potent inhibitory effect of DHP-5 on side population cancer stem cells than reference drug Verapamil.

MCF-7 treatment by DHP-5 showed an increase in Mitoxantrone accumulation which is a selective substrate to ABCG2. Indirectly it is proved that DHP-5 effects impact ABCG2 function.

Immunofluorescence staining of ABCG2 (green) and nucleus (blue) of MCF-7 cells showed that treatment with DHP-5 decreased the expression of ABCG2.

EXAMPLE 4

Antitumor Activity in Mice

Nude mice (Jackson Laboratories, Bar Harbor, Me., USA) were injected with $4*10^6$ cells of MDA-MB-468 and LOVO subcutaneously in the right flank, and tumor size was measured weekly using a caliper. When the tumor reached approximately 400 mm³ diameter, the mice were divided into control treated groups, the treatment including administration of DHP-5 (50 mg/Kg) via intraperitoneal injection daily for 14 days. The general toxicity of the treatment was determined by measuring the total body weight of the treated and control mice. The breeding, care and sacrifice of the animals were in accordance with the protocols approved by the Animal Care and Use Committee of the King Faisal Specialist Hospital and Research Centre.

Figure 2:
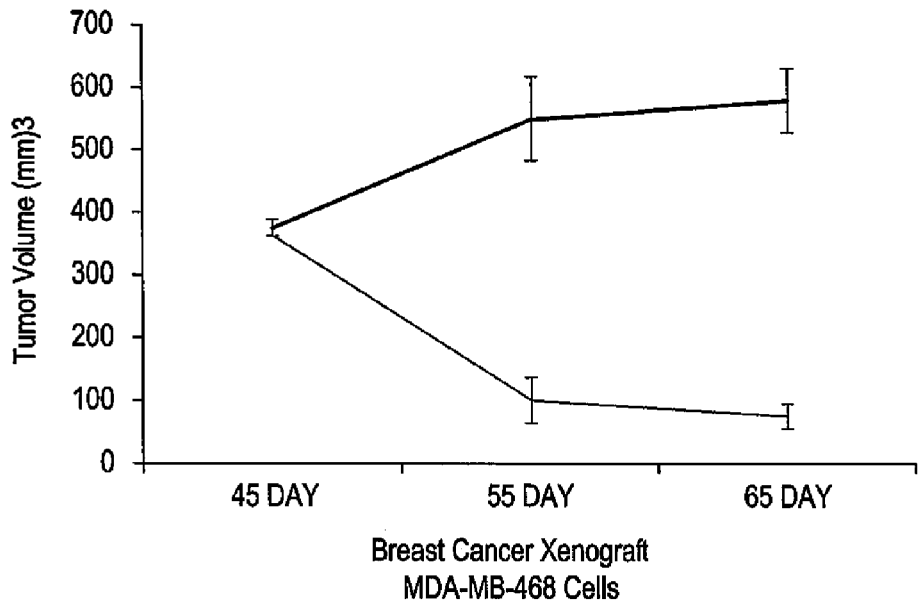
FIG. 2 is a graph showing tumor growth record of MDA-MB-468 (breast cancer xenograft) in untreated mice group (dark top line) and DHP-5 (50 mg/kg) treated mice group (light bottom line).
Figure 3:
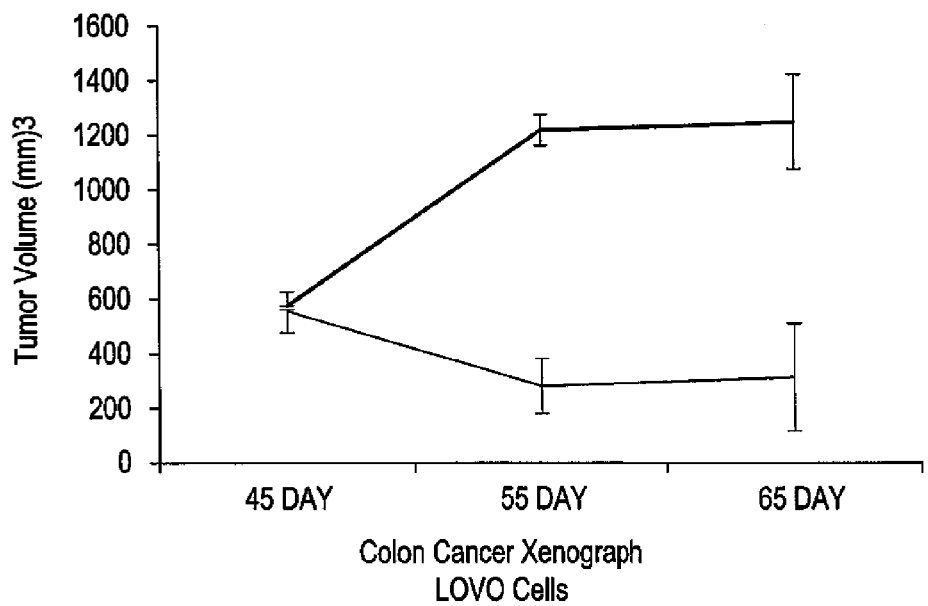
FIG. 3 is a graph showing tumor growth record of LOVO (colon cancer xenograft) in untreated mice group (dark top line) and DHP-5 (50 mg/kg) treated mice group (light bottom line).

Tumor growth of MDA-MB-468 (breast cancer xenograft) and LOVO (colon cancer xenograft) was recorded in untreated mice groups and DHP-5 (50 mg/kg) treated mice groups. Potent anti-tumor effect was demonstrated by a shrinking of tumor in the animals treated by DHP-5. Accordingly, remarkable anti-tumor effect of DHP-5 was demonstrated on tumors of breast and colon cancer xenografts (FIGS. 2 and 3).

It is to be understood that the present invention is not limited to the embodiments described above, but encompasses any and all embodiments within the scope of the following claims.

We claim:

1. A method for treating cancer using a dihydropyrimidine derivative, the method comprising administering to a patient in need thereof a pharmaceutical composition including a therapeutically effective amount of a dihydropyrimidine derivative and a pharmaceutically acceptable carrier, the cancer being breast cancer or colon cancer and the dihydropyrimidine derivative being a compound of Formula I:

FORMULA I

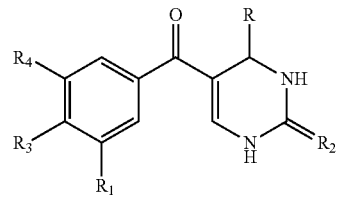

wherein:
 $R_2$ is S or O; and
 R represents phenyl, 4-Chlorophenyl, 4-Nitrophenyl, 3,4-Dimethoxyphenyl, or 4-ethoxyphenyl;
 $R_1$ represents $OCH_3$ or H; and
 $R_3$ and $R_4$ each independently represent $OCH_3$, or a pharmaceutically acceptable salt thereof wherein when $R_2$ is O, $R_1$ is $OCH_3$ and R is 4-chlorophenyl, 4-nitrophenyl or 3,4-dimethoxyphenyl; and wherein when $R_2$ is S, $R_1$ is H and R is phenyl or 4-nitrophenyl.

2. The method for treating cancer using a dihydropyrimidine derivative according to claim 1, wherein:
R is phenyl;
$R_1$ is H;
$R_2$ is S;
$R_3$ is $OCH_3$; and
$R_4$ is $OCH_3$.

3. The method for treating cancer using a dihydropyrimidine derivative according to claim 1, wherein:
R is 4-Chlorophenyl;
$R_1$ is $OCH_3$;
$R_2$ is O;
$R_3$ is $OCH_3$; and
$R_4$ is $OCH_3$.

4. The method for treating cancer using a dihydropyrimidine derivative according to claim 1, wherein:
R is 4-Nitrophenyl;
$R_1$ is $OCH_3$;
$R_2$ is O;
$R_3$ is $OCH_3$; and
$R_4$ is $OCH_3$.

5. The method for treating cancer using a dihydropyrimidine derivative according to claim 1, wherein:
R is 3,4-Dimethoxyphenyl;
$R_1$ is $OCH_3$;
$R_2$ is O;
$R_3$ is $OCH_3$; and
$R_4$ is $OCH_3$.

6. The method for treating cancer using a dihydropyrimidine derivative according to claim 1, wherein:
R is 4-Ethoxyphenyl;
$R_1$ is $OCH_3$;
$R_2$ is O;
$R_3$ is $OCH_3$; and
$R_4$ is $OCH_3$.

7. The method for treating cancer using a dihydropyrimidine derivative according to claim 1, wherein:
R is 4-Nitrophenyl;
$R_1$ is H;
$R_2$ is S;
$R_3$ is $OCH_3$; and
$R_4$ is $OCH_3$.

8. The method for treating cancer using a dihydropyrimidine derivative according to claim 1, wherein the therapeutically effective amount is from about 1 mg/kg/day to about 200 mg/kg/day.

9. The method for treating cancer using a dihydropyrimidine derivative according to claim 1, wherein the pharmaceutical composition is administered by a route of administration selected from the group consisting of intranasal administration, oral administration, inhalation administration, subcutaneous administration, transdermal administration, intradermal administration, intra-arterial administration, intracranial administration, intraventricular administration, intravenous administration, buccal administration, intraperitoneal administration, intraocular administration, intramuscular administration, implantation administration, topical administration, intratumor administration, and central venous administration.

10. The method for treating cancer using a dihydropyrimidine derivative according to claim 1, wherein the pharmaceutically acceptable carrier is selected from the group consisting of an alcohol, dimethyl sulfoxide (DMSO), a physiological saline, a lipid based formulation, a liposomal formulation, a nanoparticle formulation, a micellar formulation, a water soluble formulation, a biodegradable polymer, an aqueous preparation, a hydrophobic preparation, a lipid based vehicle, and a polymer formulation.

11. The method for treating cancer using a dihydropyrimidine derivative according to claim 1, further comprising administering to the patient an effective amount of a secondary chemotherapeutic agent, the secondary chemotherapeutic agent selected from the group consisting of paclitaxel, doxyrubicin, vinblastine, vincristine, Vinorelbine, Topotecan, Carboplatin, Cisplatin, Pemetrexed, Irinotecan, Gemcitabine, Gefitinib, Erlotinib, Etoposide, Fluorouracil, cyclophosphamide, Mercaptopurine, Fludarabine, Ifosfamide, Procarbazine, and Mitoxantrone.

* * * * *